(12) United States Patent
Morita et al.

(10) Patent No.: US 6,647,133 B1
(45) Date of Patent: Nov. 11, 2003

(54) FINGERPRINT IDENTIFICATION DEVICE-EQUIP WITH A TOUCH SENSOR FOR DETECTING A HUMAN FINGER

(75) Inventors: Takeo Morita, Kyoto (JP); Keiichi Nagayama, Kyoto (JP); Hirotaka Ishii, Kyoto (JP); Yasuhide Yomo, Kyoto (JP); Eiji Kasai, Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 09/449,555

(22) Filed: Nov. 29, 1999

(30) Foreign Application Priority Data

Dec. 10, 1998 (JP) .......................... 10-351405

(51) Int. Cl.[7] ................................ G06K 9/00
(52) U.S. Cl. ................. 382/124; 340/562; 361/179
(58) Field of Search ................... 382/124; 340/561, 340/562; 361/179, 181; 73/780

(56) References Cited

U.S. PATENT DOCUMENTS

| 3,781,855 A | | 12/1973 | Killen | |
| 4,336,998 A | * | 6/1982 | Ruell | 356/71 |
| 4,353,056 A | * | 10/1982 | Tsikos | 340/146.3 |
| 5,162,678 A | * | 11/1992 | Yamasaki | 327/331 |
| 5,465,091 A | * | 11/1995 | Nishino et al. | 341/33 |
| 5,559,504 A | | 9/1996 | Itsumi et al. | |
| 5,673,041 A | * | 9/1997 | Chatigny et al. | 341/22 |
| 5,751,835 A | | 5/1998 | Topping et al. | |
| 5,760,423 A | * | 6/1998 | Kamakura et al. | 257/99 |
| 5,760,688 A | * | 6/1998 | Kasai | 340/561 |
| 5,796,355 A | | 8/1998 | Smigelski | |
| 6,002,786 A | * | 12/1999 | Hallibert et al. | 382/124 |
| 6,107,924 A | * | 8/2000 | Kasai et al. | 340/627 |
| 6,108,438 A | * | 8/2000 | Bird et al. | 382/124 |
| 6,144,756 A | * | 11/2000 | Takahashi et al. | 382/124 |
| 6,160,904 A | * | 12/2000 | Uchida et al. | 382/124 |
| 6,259,804 B1 | * | 7/2001 | Setlak et al. | 382/124 |

FOREIGN PATENT DOCUMENTS

| EP | 0 568 342 A1 | 11/1993 |
| EP | 0 989 671 A2 | 3/2000 |
| GB | 2 241 064 A | 8/1991 |
| JP | 10-240942 | 9/1998 |
| JP | 10-307904 | 11/1998 |

* cited by examiner

Primary Examiner—Amelia M. Au
Assistant Examiner—Virginia Kibler
(74) Attorney, Agent, or Firm—Foley & Lardner

(57) ABSTRACT

A fingerprint identification device judges that the input fingerprint is identical to the fingerprint in the database only when a the touch sensor detects the human finger and a the fingerprint processing unit detects that the input fingerprint is identical to a fingerprint in the database. The touch sensor includes an oscillator that outputs a high frequency signal. An electrode unit applies the high frequency signal to the human finger. A detector unit detects a variation of impedance values varied by the human finger contracting the electrode unit and outputs an output signal based on the variation of impedance values. A discriminator unit determines whether the human finger is in contact with the electrode unit by comparing the output signal from the detector unit with a predetermined reference value.

35 Claims, 19 Drawing Sheets

BPF

HPF

LPF

FINGERPRINT IDENTIFICATION DEVICE-EQUIP WITH A TOUCH SENSOR FOR DETECTING A HUMAN FINGER

FIELD OF THE INVENTION

This invention relates generally to a fingerprint identification device to identify an individual fingerprint of a human.

BACKGROUND OF THE INVENTION

The configuration of a conventional fingerprint identification device is shown in FIG. 1. A triangle prism 2 is positioned to contact a human finger 3. An optical beam from a optical source 4 such as a Light Emitting Diode (LED) is shot from the bottom of the prism. The optical beam is totally reflected by the inclined surface of the prism 2 and it goes through the focusing lens 5. The image of the finger 3 formed on the inclined surface of the prism 2 is focused on an imaging element 6 such as a CCD (charge-coupled device).

When the finger 3 touches the inclined surface of the prism in the finger identification device mentioned above, there will be a small space despite a tight contact between the finger and the inclined surface because of the convex and concave pattern of the fingerprint. The optical beam shot to the inclined surface of prism 2 will reflect totally at the small space where the concave portion of the finger 3 contacts the prism 2, and it forms a bright image on the imaging element 6. The optical beam will pierce the inclined surface at the tight contact where the convex portion of the finger 3 contacts the prism 2, and scatter on the finger surface. It will then form a dark image on the imaging element 6. Because of there features, a fingerprint pattern having bright and dark portions is obtained on the imaging element 6.

Fingerprint identification processing unit 7 will extract features of the fingerprint from the fingerprint image formed on the imaging element 6, and compare it with a database of fingerprints of many people previously stored in the memory in order to identify the specific fingerprint.

Conventional touch sensors, however, do not have a capacity to determine whether the object touching the prism is actually a human finger. While some of the conventional inductance, electrical conductivity and high-frequency radiation based sensors are not supposed to react unless they are touched by a human finger, it is relatively easy to operate the sensors by intentionally touching them with an object having characteristics similar to a finger. That is, the conventional sensors are unable to properly discriminate human fingers from other such objects. Detecting coils, for example, detect the presence of a human body before they are actually touched, so they have a problem of accuracy in that they cannot determine whether the sensor was in fact touched by the human body.

SUMMARY OF THE INVENTION

The object of this invention is to provide a fingerprint identification device which is able to detect the touch of a human finger with improved accuracy.

In one embodiment of the invention, a fingerprint identification device to identify if the input fingerprint matches with one of a plurality of fingerprints previously stored in a database includes a touch sensor for identifying a human finger, the touch sensor including 1) an oscillator unit which outputs a high-frequency signal; 2) an electrode unit which receives the high-frequency signal from the oscillator unit and which includes electrodes that are touched by the human finger to be detected; 3) a detector unit which outputs a signal which varies with the impedance of the electrode unit; 4) a discriminator unit which determines whether the item detected is alive; and 5) a reference signal setting unit in which a reference signal is stored prior to use to determine whether the item detected is a human finger.

In this touch sensor according to the present invention, the oscillator unit supplies a high-frequency signal to the electrode unit. If the item detected is a biological entity of a human body such as a finger, then the impedance of the electrode unit will change. The impedance is initially set to the impedance on the input side of the electrode when the finger is touching the electrodes. The reflected wave will be smaller due to the change in impedance when the finger is touching the electrodes. By detecting this reflected wave and comparing it with a reference signal in the discriminator unit, it can be determined that the reflection level is lower and that the electrodes are being touched by a person, but not an imitation finger.

The fingerprint identification unit according to this invention will determine that the input fingerprint is identical to the fingerprint in the database only when the touch sensor detects a human finger and the fingerprint processing unit detects the input fingerprint is identical to the fingerprint in the database. This feature will prevent cheating by using an imitation finger to ensure the accuracy of fingerprint detection.

BRIEF DESCRIPTION OF THE DRAWINGS

The accompanying drawings, which are incorporated in and constitute a part of the specification, illustrate presently preferred embodiments of the invention, and, together with the general description given above and the detailed description of the preferred embodiments given below, serve to explain the principles of the invention.

DETAILED DESCRIPTION OF THE PREFERRED EMBODIMENTS

Figure 1:
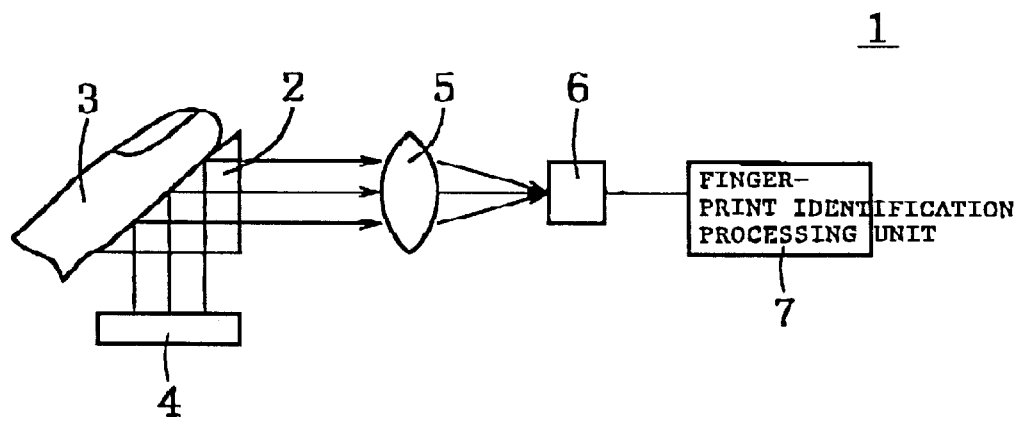
FIG. 1 is a block diagram of a conventional fingerprint identification device.
Figure 2:
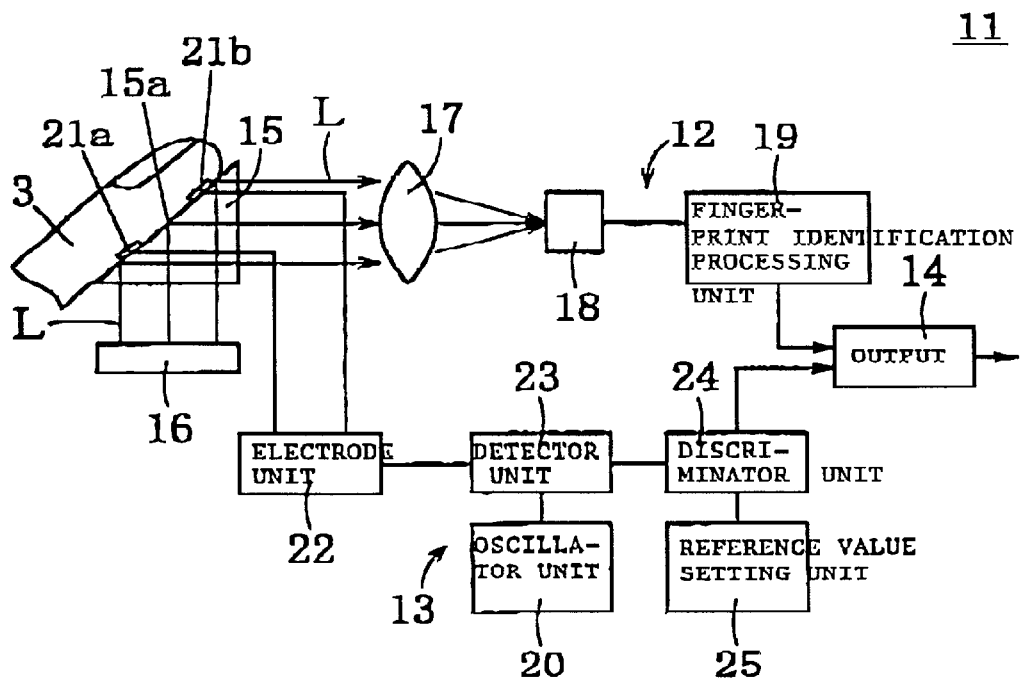
FIG. 2 is a block diagram of one embodiment a fingerprint identification device equipped with a touch sensor for detecting a human finger according to the present invention.

The configuration of the first embodiment of the present invention is shown in FIG. 2. The fingerprint identification device 11 has a fingerprint identification unit 12, a touch sensor 13 to detect the touch of a human finger, and an output unit 14. The fingerprint identification unit 12 includes right angle triangle prism 15, one or more light sources 16 such as a LED and the alike, an imaging element 18 such as a CCD or the like, a focusing lens 17 to focus the image at an inclined surface 15a of prism 15 on an imaging element 18, and a fingerprint processing unit 19, such as a programmed micro computer (CPU) to identify the fingerprint.

Optical beam L is shot from the light source 16 to the bottom of the prism 15. The light entered from the bottom of prism 16 is totally reflected by the inclined surface 15a, and exits from the side of prism 15. The optical beam L exiting from the side of the prism 15 enters imaging element 18 through the focusing lens 17, and the image on the inclined surface 15a is focused on the imaging element 18.

If a human finger 3 touches the inclined surface 15a, a small space (air space) is created between the concave portion of the fingerprint pattern and the inclined surface 15a. Because of this air space, the optical beam will be reflected totally by the inclined surface and exit from the side of the prism 15. In contrast, the convex portion of the fingerprint will tightly contact the inclined surface 15a, and the optical beam L entered on this portion will pierce the inclined surface and scatter on the finger 3. The concave portion of the fingerprint, therefore, forms a bright image on imaging element 18, and the convex portion of the fingerprint forms a dark image on imaging element 18. The above describes the principle of forming a fingerprint pattern on the imaging element 18 according to the present invention.

Imaging element 18 converts the optical information to electrical information. The fingerprint pattern (bright and dark patterns) formed on imaging element 18 is sent to the fingerprint processing unit 19 as digitized data. Fingerprint processing unit 19 analyzes the digital data received from imaging element 18 to extract a feature amount of the fingerprint and generate fingerprint data. The fingerprint data includes a direction of flow, number of central cores, and distance between the central cores, and other fingerprint features that are well known (Japanese patent publication, Kokai 5-61964). Fingerprint processing unit 19 has a fingerprint data base in a memory unit, and compares the individual fingerprint formed on the inclined surface 15a against the fingerprints in the data base for identification. If fingerprint processing unit 19 detects a fingerprint pattern which is identical to a fingerprint in the data base, it judges that the fingerprint on the inclined surface 15a is a target fingerprint to be checked out.

Figure 3:
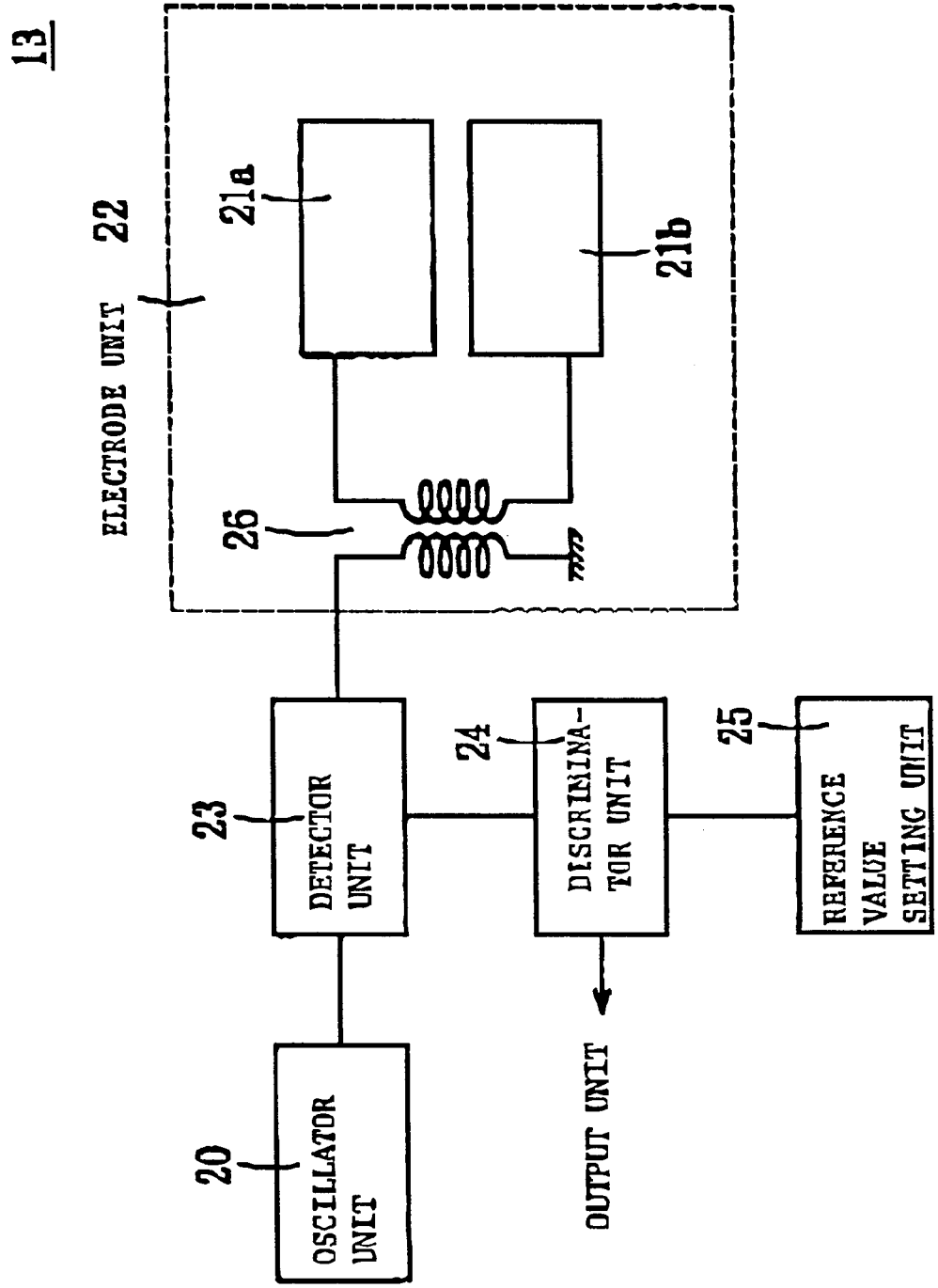
FIG. 3 is an exemplary block diagram of a touch sensor according to the present invention.

FIG. 3 is an exemplary block diagram of a touch sensor according to the first preferred embodiment of the present invention. The touch sensor 13 of this embodiment is designed to detect whether it has been touched by a finger. The touch sensor comprises 1) an oscillator unit 20 which generates and emits a high-frequency signal, 2) an electrode unit 22 which includes a pair of electrodes 21a and 21b and a transformer 26 that is used for an impedance comparison, 3) a detector unit 23 which detects the level of the high-frequency signal supplied by oscillator unit 20 to electrode unit 22 and reflected by it, and 4) a discriminator unit 24 which determines from the amplitude of the detected signal whether the touch sensor is touched by a finger.

In the touch sensor 13 for human finger, the high-frequency signal is supplied from the oscillator unit 20 to the electrode unit 22. Since the electrode unit 22 is set so that a comparison of impedance matches only when a finger is touching the pair of electrodes 21a and 21b, the high-frequency signals from oscillator unit 20 flow into the secondary side of transformer 26 without reflecting on the electrodes if a human finger actually touches the electrodes 21a and 21b. On the contrary, if an object other than a human finger, such as an imitation finger, touches the electrodes 21a and 21b, the comparison of impedance does not match, and a detecting signal representing such an imitation finger is generated. The detecting signal is, for example, reflection signal from electrode unit 22, and the high-frequency signal will not be transmitted to the electrode unit 22. By detecting whether there is a reflection signal reflected at electrode unit 22 or not, or by comparing the reflection level with the reference value set in reference value setting unit 25, it is possible to detect if the object in touch with the electrodes is an actual human finger or an imitation finger by discriminator unit 24. The touch sensor 13 is described below in greater detail.

FIG. 3 is an exemplary block diagram of the touch sensor 13 according to the first preferred embodiment of this invention. The touch sensor 13 of this embodiment is designed to detect whether it has been touched by a human finger. The touch sensor 13 comprises an oscillator unit 20 which generates and emits a high-frequency signal, an electrode unit 22 which includes a pair of electrodes 21a and 21b and a transformer 26 that is used for an impedance comparison, a detector unit 23 which detects the level of the high-frequency signal supplied by the oscillator unit 20 to the electrode unit 22 and reflected by it, and a discriminator unit 24 which determines from the amplitude of the detected signal whether the touch sensor 13 is touched by a finger. Reference value setting unit 25 sets the reference impedance value to discriminate the human touch to the electrode unit 22.

Since this embodiment of a touch sensor can be used both as a touch sensor, when combined with a light, and in a fingerprint identification device, the electrodes must allow light to pass through. The transmissivity of electrodes 21a and 21b is therefore specified to be greater than 50%. For this purpose, an ITO membrane can be used for electrodes 21a and 21b.

If it is not necessary for light to pass through electrodes 21a and 21b, they can be made of a material which is a good conductor of high-frequency radiation. This is important if the electrodes are long. Materials which are good high-frequency conductors include, for example, silver, gold, copper and aluminum. If electrodes 21a and 21b need not be translucent and they are to be relatively short, then detection can be accomplished by the use of semiconductors.

Figure 5:
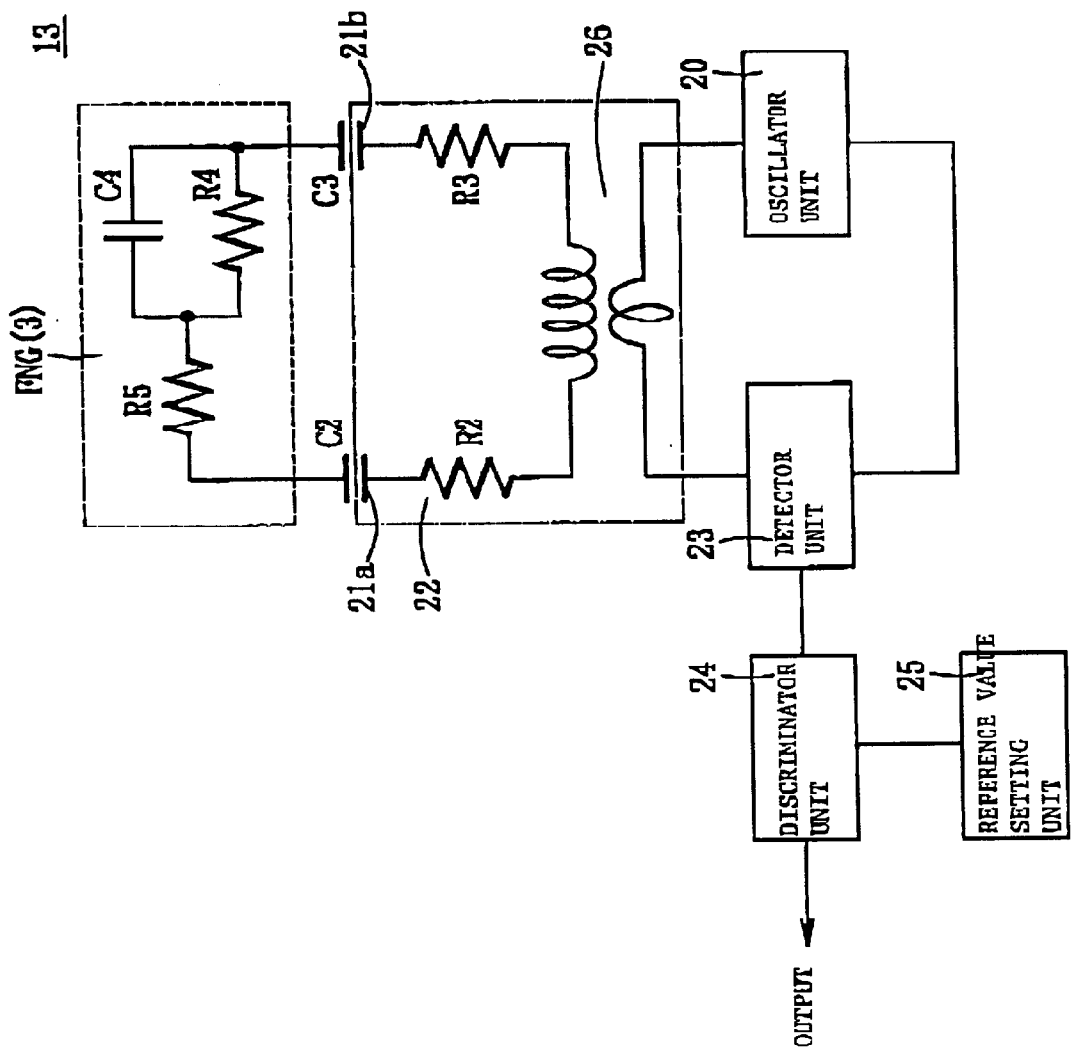
FIG. 5 is an exemplary diagram of an equivalent circuit which illustrates the principle of detection used in the touch sensor shown in FIG. 2.

FIG. 5 is an exemplary diagram of an equivalent circuit that illustrates the principle of detection used in the touch sensor 13 in FIG. 3. When a finger is not touching the area between electrodes 21a and 21b, respectively, the secondary side of transformer 26 is in an open state. When the area between electrodes 21a and 21b is touched, the resistance values $R_2$ and $R_3$ of electrodes 21a and 21b, the capacitance values $C_2$ and $C_3$ between electrodes 21a and 21b and the finger, and the equivalent circuit FNG of the finger, which includes a capacitor $C_4$ and resistors $R_4$ and $R_5$, are serially connected to the secondary coil of transformer 26. When a finger touches the area between electrodes 21a and 21b, the capacitance between the finger and electrodes 21a and 21b increases and the high-frequency impedance value of the finger is compared to the reference value. Using this principle, the discrimination unit 24 determines whether the touch is that of a finger. The impedance measured on the secondary side of transformer 26, when a finger touches the electrodes, can be used as a criterion for comparison. The level of the high-frequency signal from oscillator unit 20, after it is reflected by electrode unit 22, determines whether the sensor has been touched by a finger. As an example, if the resistance value $R_4+R_5$ of the finger is approximately 40Ω, the resistance value $R_2+R_3$ is approximately 30Ω, the capacitance when the finger is touching the electrodes is approximately 3000 PF, and the reactive component ½ πfc of capacitance C is 1.3Ω (40.68 MHz), then the total impedance is 102.6Ω. If the transformer 26 is set at approximately 50:100, the resulting impedance at the first side of the transformer 26 will be approximately 50Ω when a finger is touching the sensor, and the comparison of impedance will match at both sides of the transformer. If the transformer is set so that the comparison of impedance will match only when a finger touches the sensor, then the comparison of impedance will not match when an object other than a finger touches the sensor since it will have a different impedance value. If the item detected does not come in contact sufficiently with the electrodes, then the capacitance will drop, and the reactive component of C will increase, and as a result, the comparison of impedance values will not match. When the capacitance drops at this time, the imaginary component of the impedance will increase. Thus, even if the comparison of resistance components matches, the imaginary portions of the impedance would not match with each other, and then the touch sensor would not recognize the object as a finger.

In the touch sensor to detect the human finger touch according to the present invention, the following two conditions must be satisfied. First, the capacitance between electrodes 21a, 21b and the finger must increase significantly when the finger comes in close contact with the electrodes, and the capacitance must be within a reference value. Second, because the high-frequency impedance value of the finger is different from other materials, the resistance component must be within the predetermined range. In order to detect the changes above, the oscillator unit 20 of the touch sensor supplies a high-frequency signal to the electrode unit 22. If the item detected is a biological entity of a human body such as a finger, then the impedance of the electrode unit changes. The impedance is initially set to the impedance on the input side of the electrode when the finger is touching the electrodes. The reflected wave is smaller due to the change in impedance when the finger touches the electrodes. By detecting this reflected wave and comparing it with a reference signal in the discriminator unit, it can be determined that the reflection level is lower and that the electrodes are being touched by a human finger.

The finger identification device according to the present invention is equipped with the touch sensor mentioned above, and the device detects a finger under the following two conditions: (1) the item makes contact with the electrodes just as a finger does, and (2) it has the same impedance component as a finger. These requirements keep false positives to a minimum. The device is virtually immune to electromagnetic fields. The device employs ISM frequency, so it is not subject to laws governing radio or is it affected by radio interference. The device can run on 1 mW of electricity, so it has no adverse effects on human beings. Other benefits may also be realized.

The electrodes 21a and 21b, which enable the touch sensor to detect a finger in the embodiment discussed above, are symmetrically disposed to the left and right with a gap of 1 mm in between. They may be of various shapes, such as rectangular, semi-cylindrical, elliptical, circle, half-circle, triangular, sword-shaped, crescent-shaped and the like.

Figure 4A:
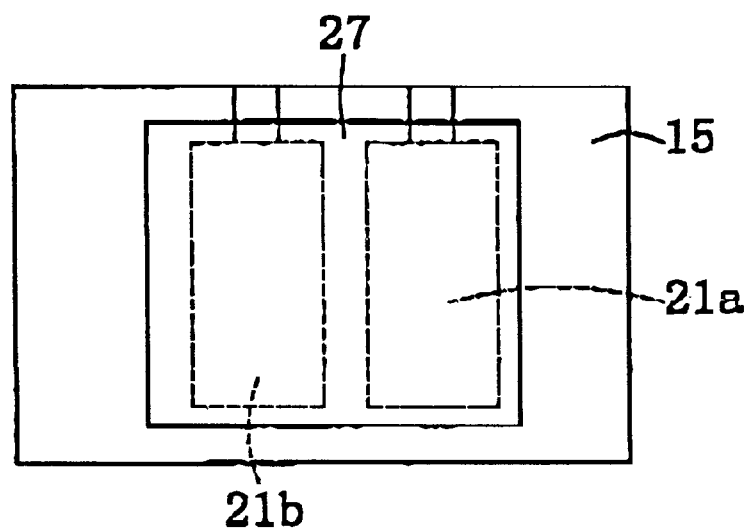
FIGS. 4(a) and 4(b) illustrate an exemplary configuration of the electrodes used in the above embodiment.
Figure 4B:
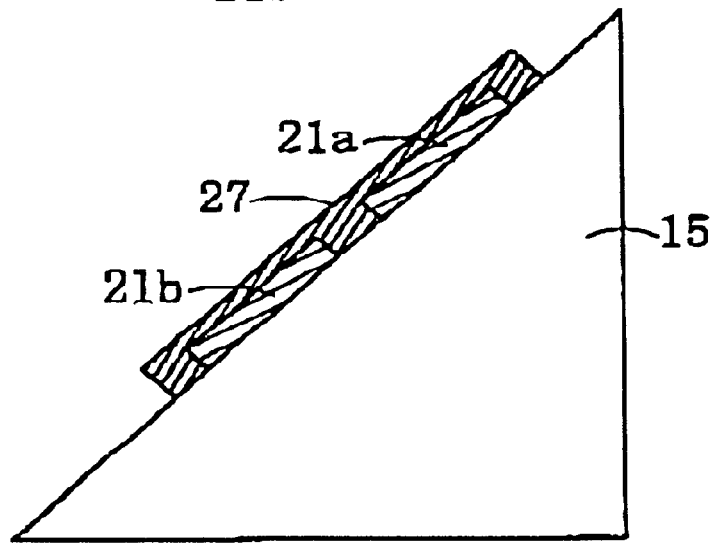

FIG. 4 is a graph of the relationship between the frequency and the reflected wave amplitude under the different conditions. The values are set so that a comparison of the impedance values match only when a finger is touching the electrodes. Since the level of the reflected wave is set quite low when the thumb or little finger touches the detector, the threshold value of discriminator unit 24 should be set somewhat higher than the detected level for the little finger. This will ensure that discriminator unit 24 can detect the touch of a finger accurately.

Figure 7:
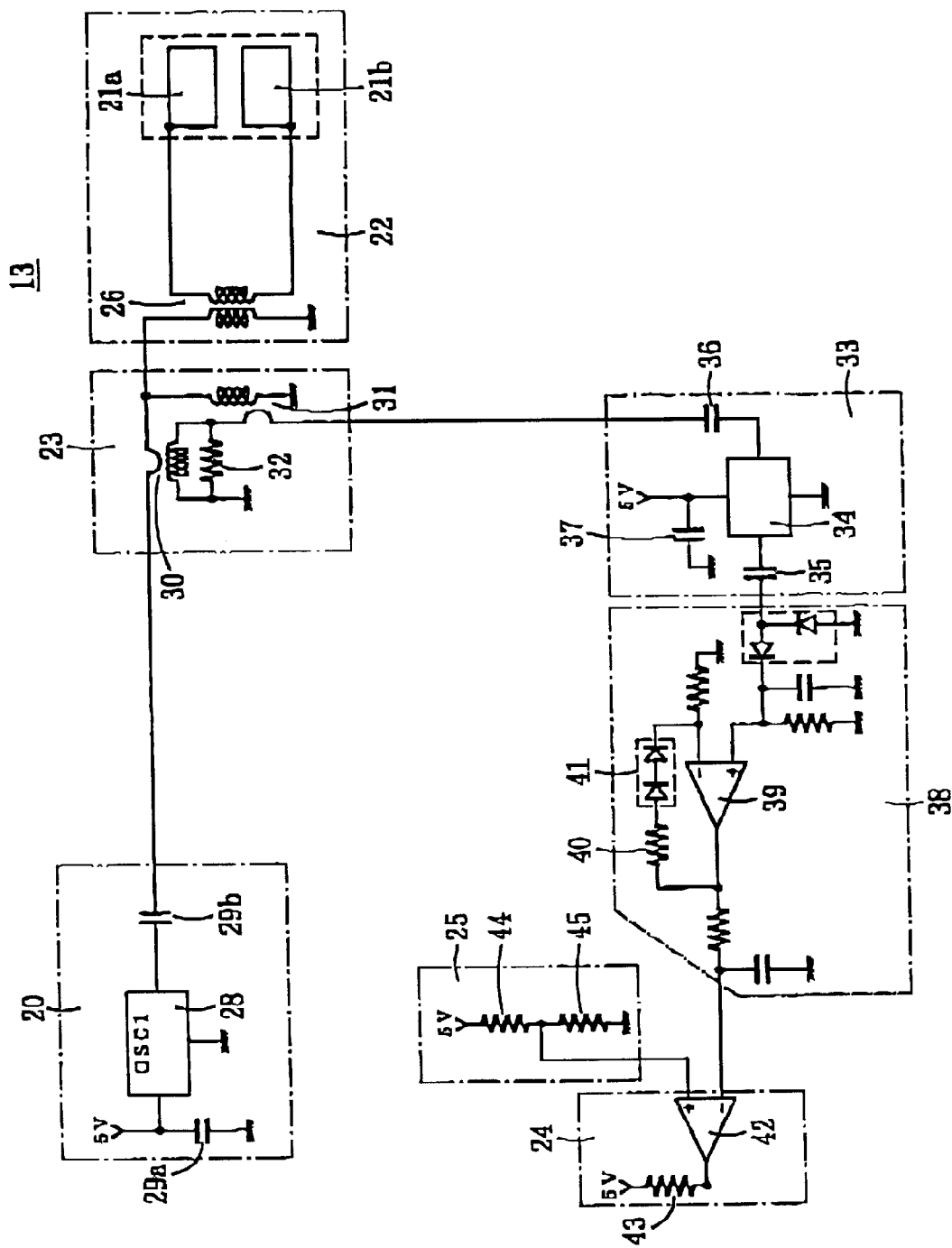
FIG. 7 illustrates an electric circuit for the touch sensor.

FIG. 7 illustrates an exemplary circuit for the finger identification device. Oscillator 20 comprises an oscillator IC 28, and 5 volt DC is supplied to oscillator IC 28. In order to stabilize the voltage of the DC power, condenser 29a for stabilizing the voltage is inserted between the in-port of oscillator IC 28 and the ground. High-frequency signal is supplied from oscillator IC 28 to detector unit 23 through condenser 29b which eliminates the DC portion. Electrode unit 22 comprises a pair of electrodes 21a and 21b, and a transformer 26 which supplies power and matches impedance value. Electrodes 21a and 21b are connected on the secondary side of the transformer 26. Electrode unit 22 closes the circuit when a human finger comes in touch with electrodes 21a and 21b. The impedance value at a first side of the transformer 26 and the reflection wave is minimized when a human finger makes contact with the pair of electrodes. On the other hand, the comparison of the impedance will not match and the reflection wave will increase when an imitation finger or phony finger comes in touch with the pair of electrodes 21a and 21b.

Detector unit (reflection sensor) 23 comprises two sets of transformers 30, 31, and a resistor 32. The first coil of transformer 30 is serially connected between oscillator 20 and electrode unit 22. The first coil of transformer 31 is connected between the output terminal and the ground. One terminal of the secondary coil of transformer 30 is connected to the ground, and resistor 32 is connected in parallel to the secondary coil of transformer 30. The secondary coil of transformer 31 is connected in series with the secondary coil of transformer 30. The output terminal of the secondary coil of transformer 31 (terminal for taking out the reflection wave) is connected to high-frequency amplifier circuit 33. With the circuit configured as above, the signal level generated at the first sides of the transformers 30, 31, which is dependent on the impedance matching level at electrode unit 22, is collected at the secondary sides of the transformer 30, 31. If a human finger touches electrode unit 22, the reflection wave from the electrode unit 22 is small and the output signal level from detector unit 23 will be low because the circuit is set so that the impedance is matching. On the other hand, if the object in touch with the electrode unit 22 is an imitation finger, the impedance will be not be matching, and the reflection wave from electrode unit 22 will be large and the output signal level from detector unit 23 will be high.

High-frequency amplifier circuit 33 comprises high-frequency amplifier IC (for example, UPC1676), condensers 35, 36 for eliminating DC, condenser 37 for stabilizing the voltage. After high-frequency amplifier circuit 33 amplifies the high-frequency input from detector unit 23, it is output to the next unit, demodulation amplifier circuit 38. Demodulation amplifier circuit 38 comprises operational amplifier 39, resister 40 and diode 41 in a negative feed back circuit provided between the output terminal and the reversing input terminal of the operational amplifier 39. Demodulation amplifier circuit 38 detects the high-frequency signal amplified in the high-frequency amplifier circuit 33, and amplifies it further.

Discriminator unit 24 comprises comparator 42, and a 5 volt power source is supplied to the output side of the comparator 42 through a pull-up resister 43. The output terminal of demodulation amplifier circuit 38 is connected to the reversing input terminal of comparator 42, and the non-reversing input terminal of comparator 42 is connected to a reference value setting unit 25. In the reference value setting unit 25, the divided voltage generated by dividing 5 volts by two divider resisters 44, 45 is supplied to comparator 42 in discriminator unit 24. The reference value (voltage) can be adjusted by changing the value of these two divider resisters 44, 45. When the DC voltage output from demodulation amplifier circuit 38 is lower than the reference voltage supplied from reference value setting unit 25, the discriminator unit 24 will output a H (high) signal. When the DC voltage output from demodulation amplifier circuit 38 is higher than the reference voltage supplied from reference value setting unit 25, discriminator unit 24 will output a L (low) signal.

Figure 6:
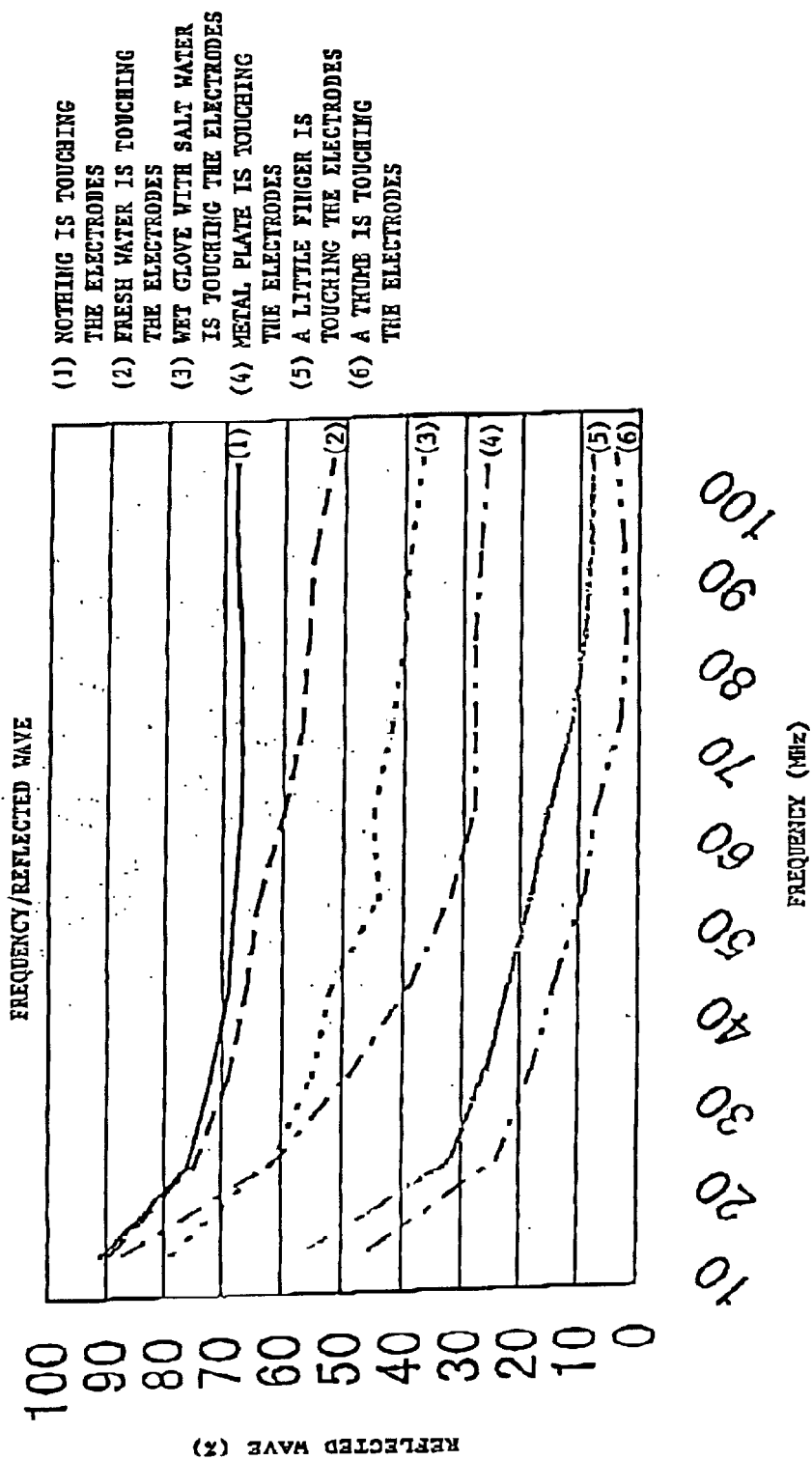
FIG. 6 illustrates an exemplary graph of the relationship between the frequency and the reflected wave amplitude.

If the reference voltage value (threshold value) set by reference value setting unit 25 is set at the reference DC voltage which is a little higher than the output DC voltage from detector unit 23 when the human finger is in touch with electrodes 21a, 21b (see FIG. 6), then discriminator unit can discriminate the human finger from an imitation finger. When the human finger touches electrodes 21a, 21b, the discriminator unit 24 will output the High-signal. When the imitation finger touches electrodes 21a, 21b, the discriminator unit 24 will output the Low-signal.

The setting of High-signal and Low-signal can be reversed for detecting an imitation and detecting a human finger respectively. In this embodiment, discriminator unit 24 uses a comparator including an operational amplifier. It is, however, possible to use a comparator including transistors and discrimination is done by a programmed microcomputer (CPU).

As shown in FIG. 2, when fingerprint processing unit 19 in fingerprint identification unit 12 identifies the fingerprint previously registered in the fingerprint data base, and touch sensor 13 detects the touch of a human finger, output unit 14 will output the control signal to a following processing unit (not shown). The following processing unit mentioned here can be, for example, control units for door control devices, automobile door locks, or ignition systems, and these processing units can open house doors, automobile doors, or even start an automobile.

Figure 8:
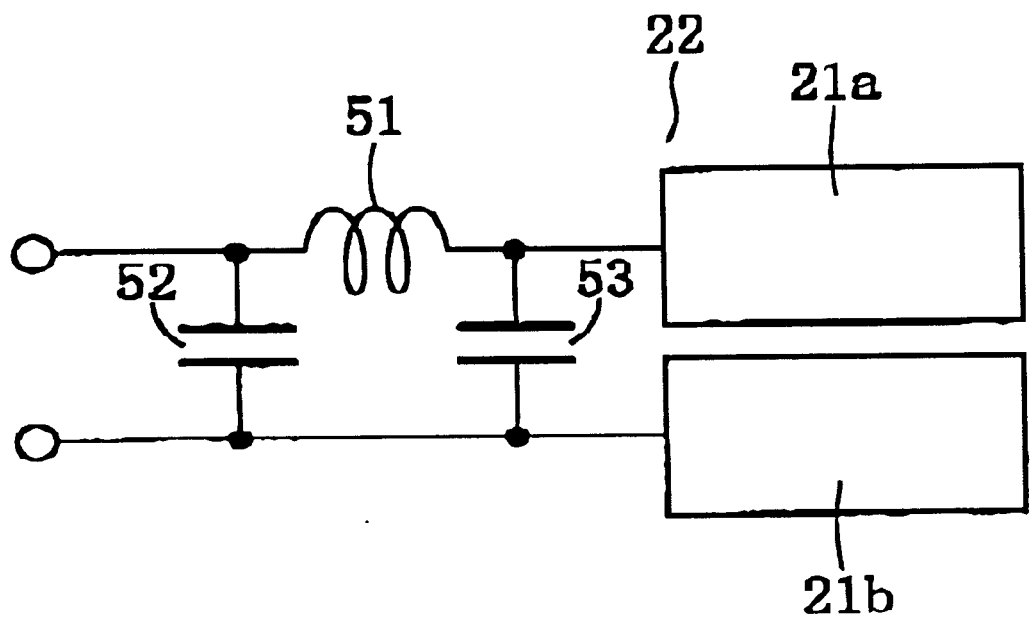
FIG. 8 illustrates another exemplary circuit for the electrodes.

As illustrated in FIG. 7, transformer 26 is used to match the impedance between electrodes 21a, 21b and the supply side of oscillator unit 20. Alternatively, in a second preferred embodiment as shown in FIG. 8, a π—type impedance converter circuit comprising capacitors C 53 and C 53 and coil 51 may be used. Although they are not shown in the drawings, a T-type or L-type impedance converter circuit, for example, may also be used for impedance matching.

Figure 9:
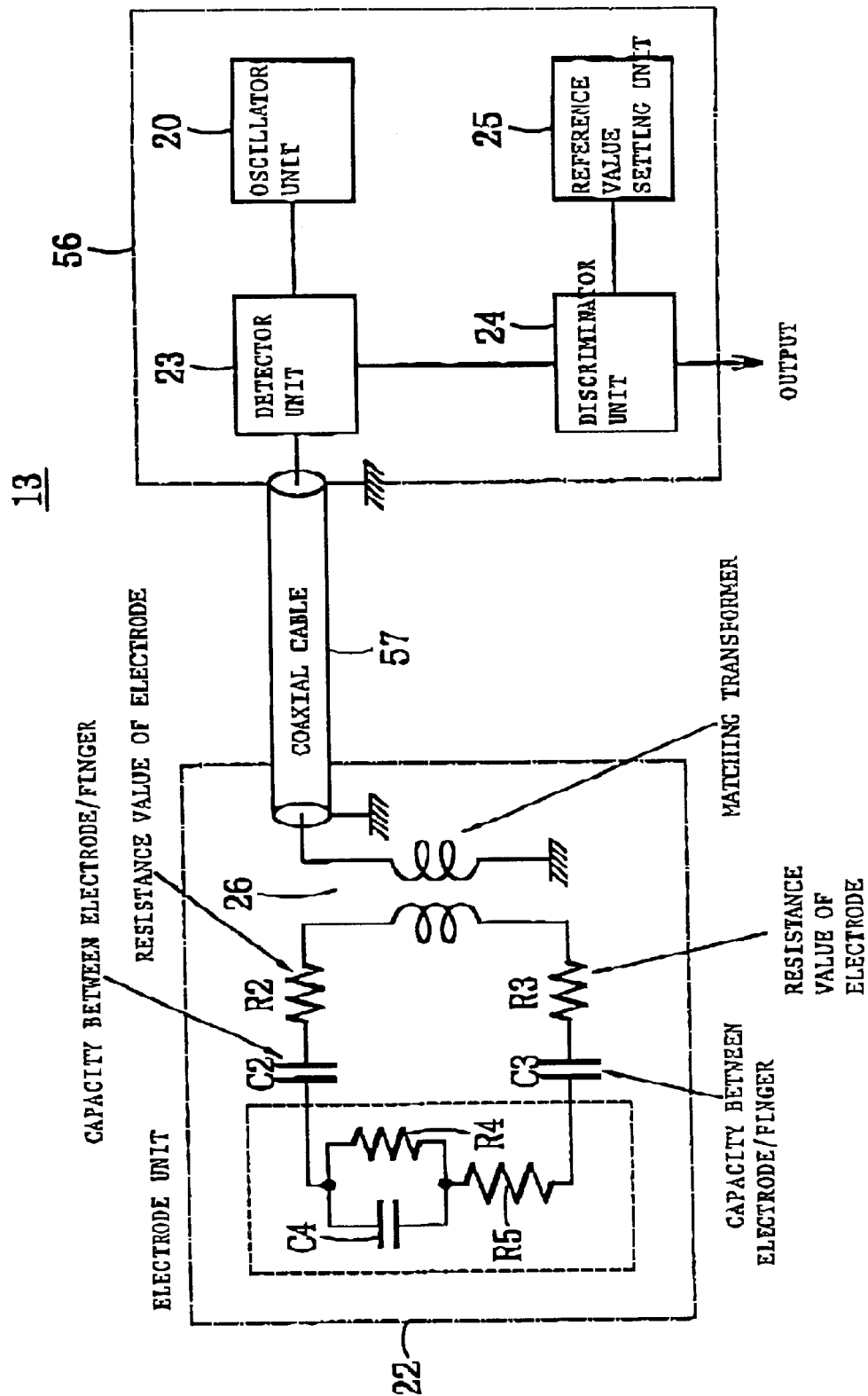
FIG. 9 illustrates a block diagram of another embodiment of to the present invention.

In the embodiment of the touch sensor discussed above, electrode unit 22, as well as the circuitry for oscillator unit 20, detector unit 23 and discriminator unit 24 are all housed in a single case. In a third embodiment, as shown in FIG. 9, the electrode unit 22 and a circuit unit 56 are provided as separate entities which are connected by a cable 57, forming a detached-type touch sensor. In this case, circuit unit 56 contains oscillator unit 20, detector unit 23 and discriminator unit 24. This arrangement can prove helpful when the space for the touch sensor is limited. In this detached-type touch sensor, a coaxial cable 57 is used for the connecting cable, and transformer 58 is housed in electrode unit 22.

Figure 10:
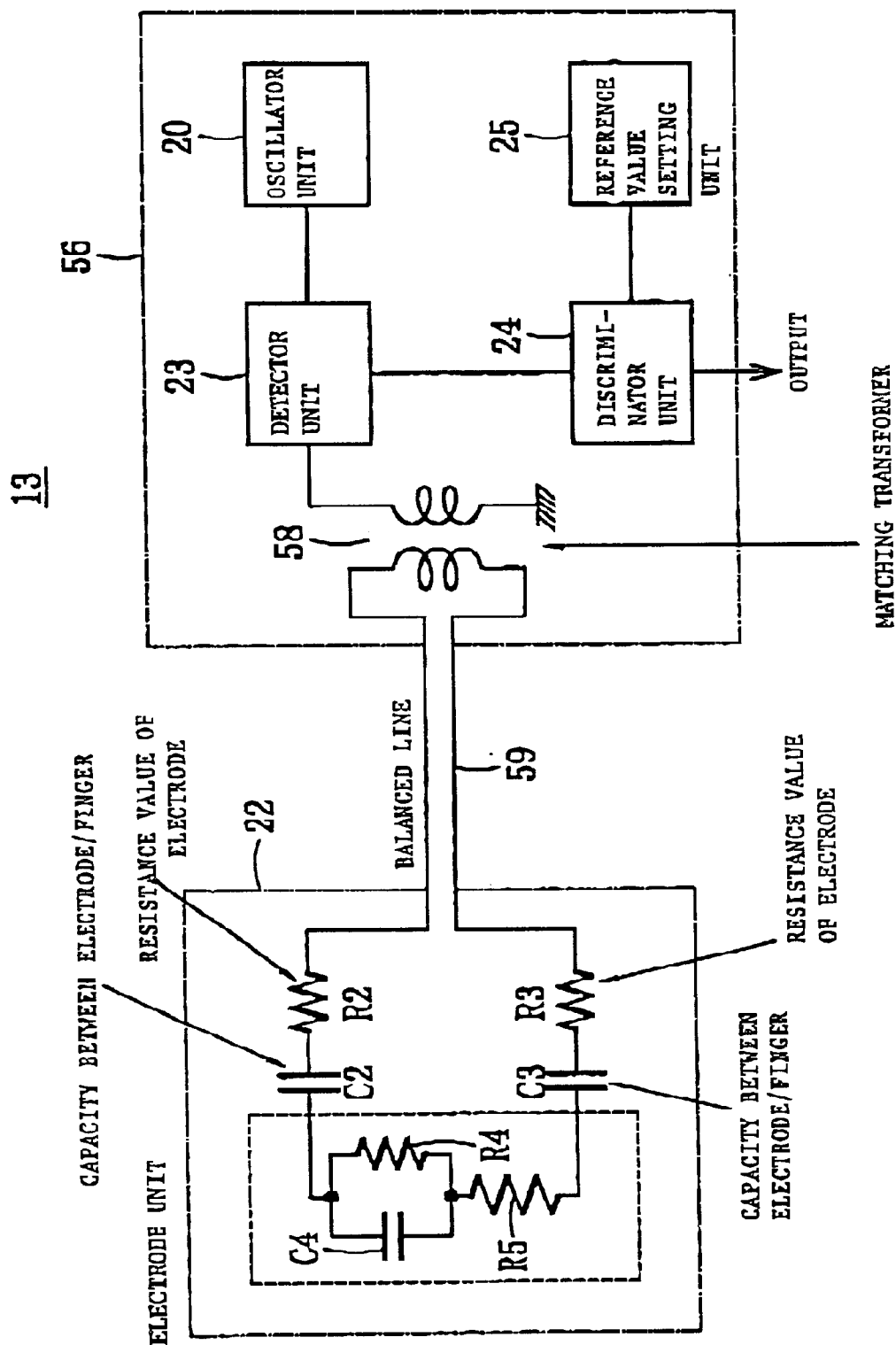
FIG. 10 illustrates a block diagram of another embodiment of the present invention.

FIG. 10 is an exemplary block diagram of another circuit layout for a detached-type touch sensor. In this touch sensor, a balanced line is used as cable 59, and the design differs from that shown in FIG. 9 in that transformer 58 is placed in circuit unit 56.

Figure 11:
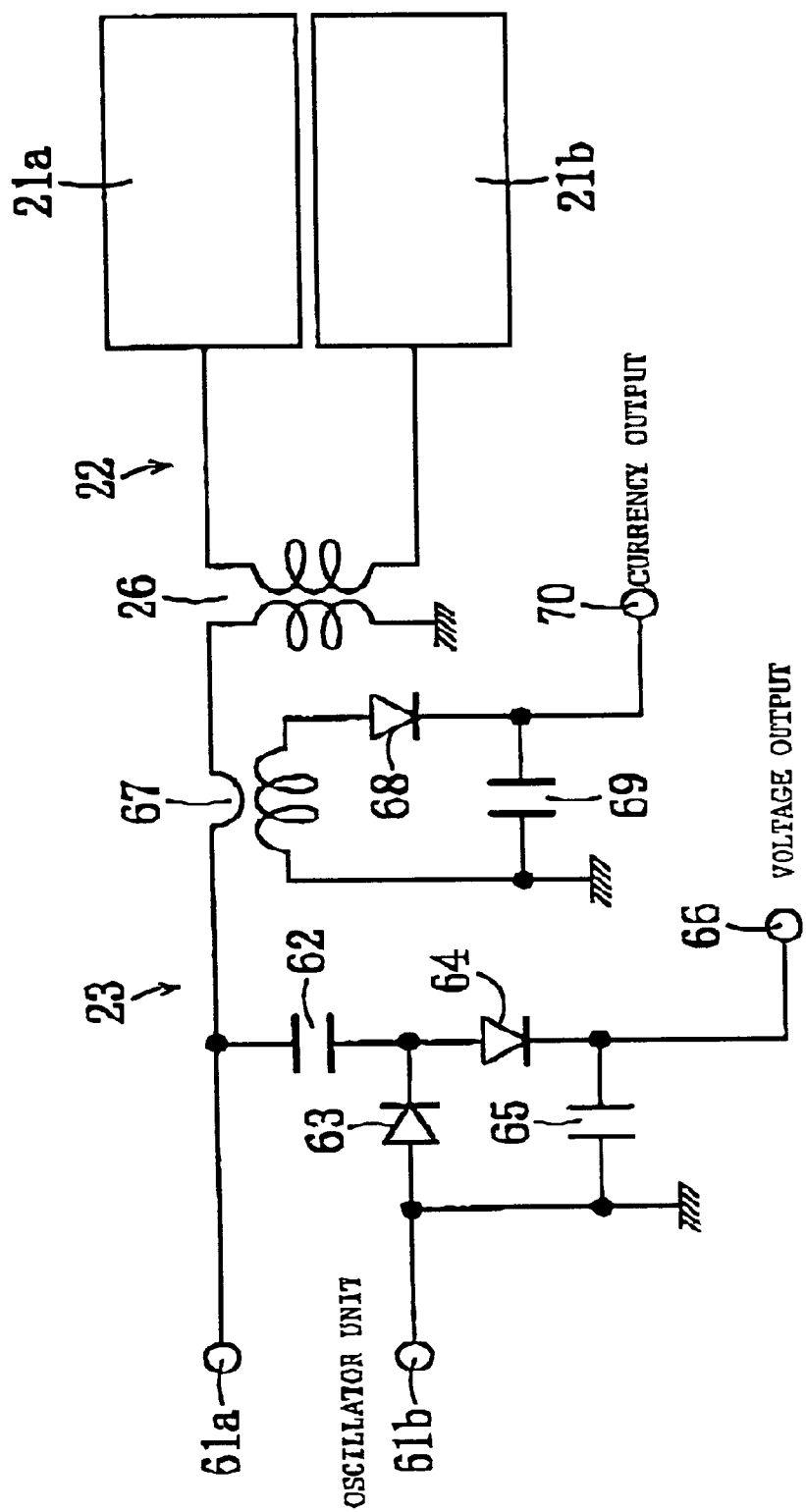
FIG. 11 illustrates another embodiment of the circuit diagram according to the present invention.
Figure 16:
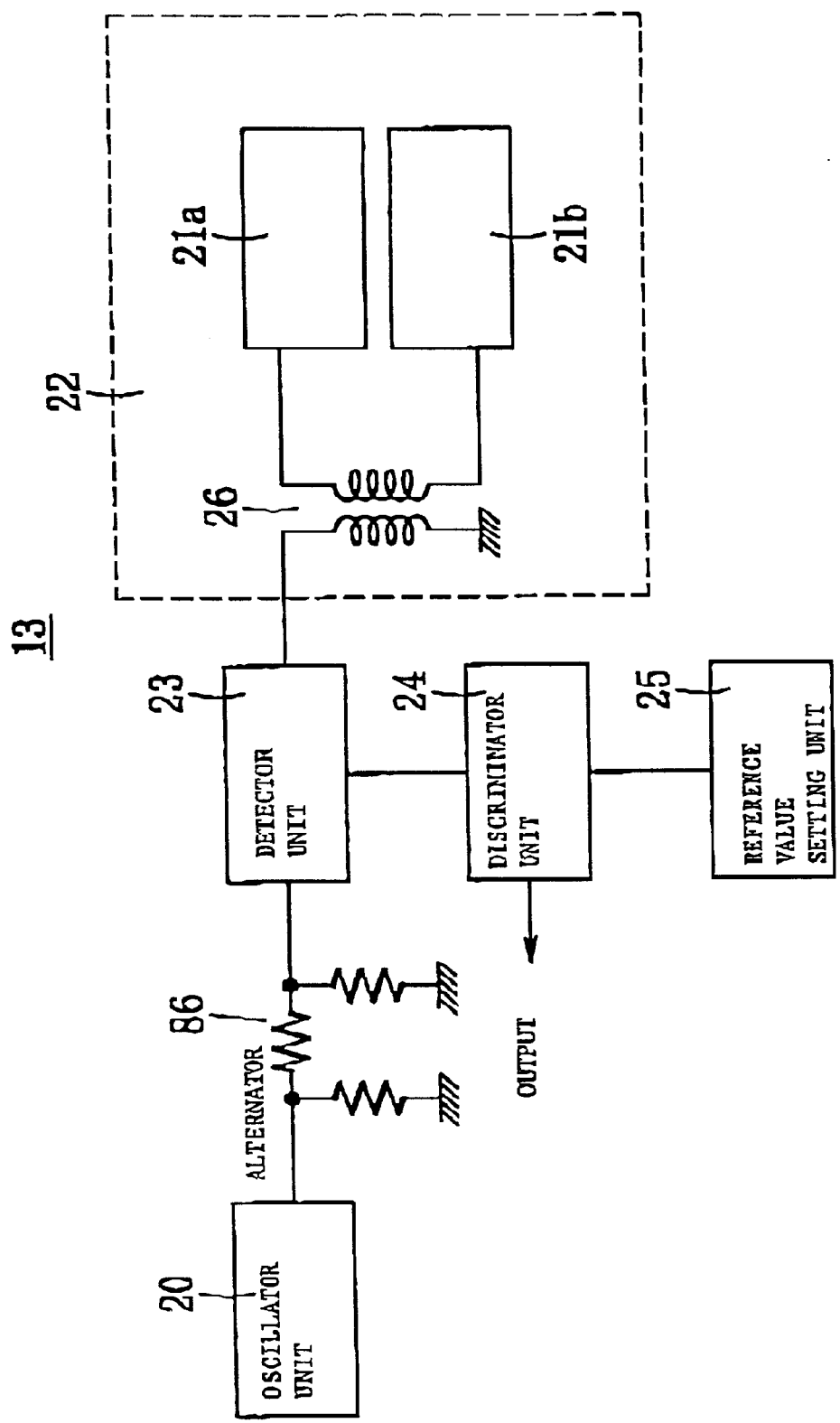
FIG. 16 illustrates a block diagram of another embodiment of the present invention.

FIG. 11 illustrate a fourth preferred embodiment of the present invention. Detector unit 23 may also detect the voltage and current of the power supplied to electrode unit 22. FIG. 16 shows an example of such a circuit. In FIG. 16, an oscillator unit 20 is connected to terminals 61a and 61b (shown in FIG. 11). One end of capacitor 62 is connected to terminal 61a and the other to the cathode of diode 63 and the anode of diode 64. The anode of diode 63 is connected to the ground. The cathode of diode 64 is connected to one end of a capacitor 65 and to output terminal 66. The other end of capacitor 65 is connected to the ground. The voltage output is obtained from output terminal 66.

One end of the primary winding of M coupling coil 67 is connected to terminal 61a. The other end of the primary winding is connected to transformer 26 of electrode unit 22. The anode of diode 68 is connected to one end of the secondary winding of M coupling coil 67, the other end is connected to the ground. The cathode of diode 68 is connected to one end of capacitor 69 and to output terminal 70, while the other end of capacitor 69 is connected to ground. The current output is obtained at output terminal 70. Alternatively, the output of only one of the voltage or current may be obtained. In this embodiment, M coupling coil 67 is used, but MM coupling or CM coupling coil is also acceptable.

Figure 12:
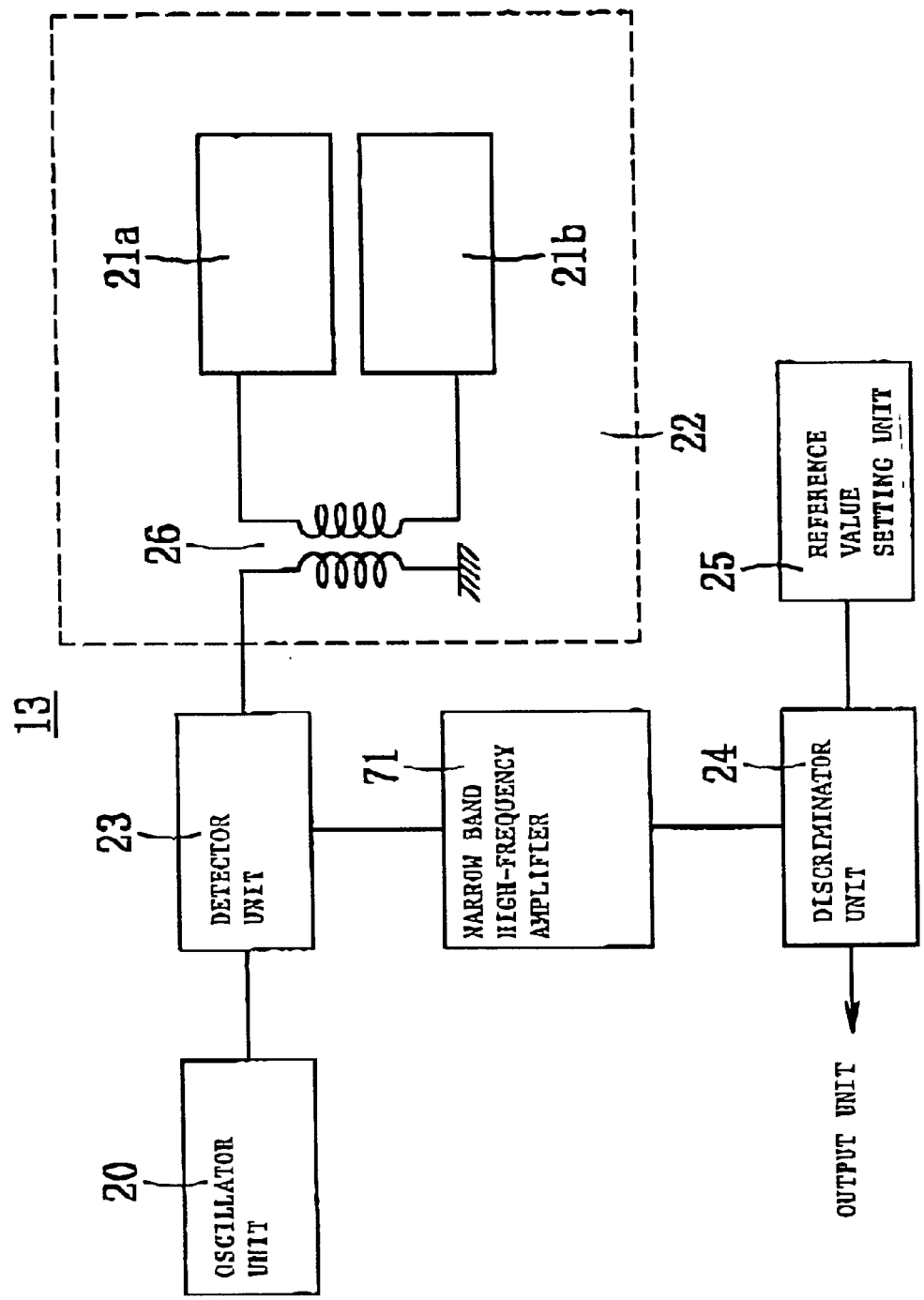
FIG. 12 illustrates a block diagram of another embodiment of the present invention.

FIG. 12 shows a fifth preferred embodiment according to the present invention. Generally, detector unit 23 detects the wave, immediately converts it to DC and amplifies it with an operational amplifier or the like. To reduce costs, a low-priced operational amplifier with a single power supply may be used, setting the amplification factor higher. In this regard, the offset voltage of the operational amplifier would be amplified and the offset voltage of the output voltage would be higher. This would adversely affect the resolution of the control unit (i.e., the discriminator unit 24). To address this problem, a narrow band high-frequency amplifier 71 is provided directly after detector unit 23, as shown in FIG. 12. Because the voltage is high after the wave is detected and converted to DC, an operational amplifier with a lower amplification factor can be used. It is also possible to dispense with the amplifier altogether. In this way the resolution of the sensor can be enhanced.

Depending on the environment in which the sensor is used, external noise from electrode unit 22 may enter the circuit and cause the sensor to malfunction. If noise gets into the output voltage of detector unit 23, it will have a significant effect on the output of the sensor. To improve the immunity of the sensor to such noise, a filter is provided in high-frequency amplifier 71 to reduce other frequency components. Since the output waveform of detector unit 23 is shaped by the filter, the high-frequency component is reduced and the accuracy of the touch sensor 13 is improved.

Figure 13:
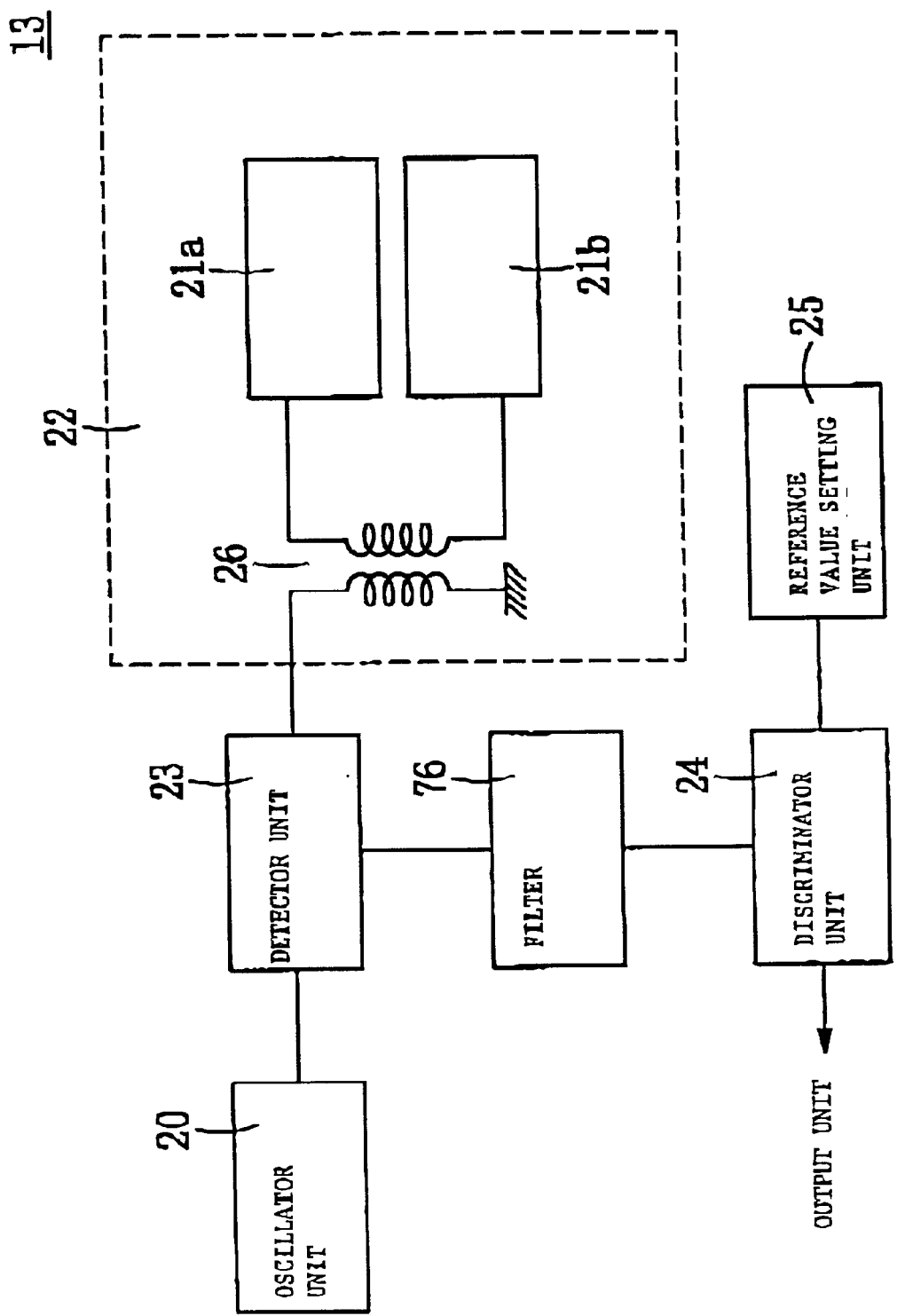
FIG. 13 illustrates a block diagram of another embodiment of the present invention.

FIG. 13 shows a sixth preferred embodiment of the finger identification device according to the present invention. A filter 76 at the frequency of use is placed between detector unit 23 and discriminator unit 24. Thus, even if other frequency components intrude from electrode unit 22, they are eliminated by the filter. This prevents the sensor from malfunctioning. Also, since a signal at the frequency of use is selectively received, the sensitivity of the sensor is improved.

Figure 14C:
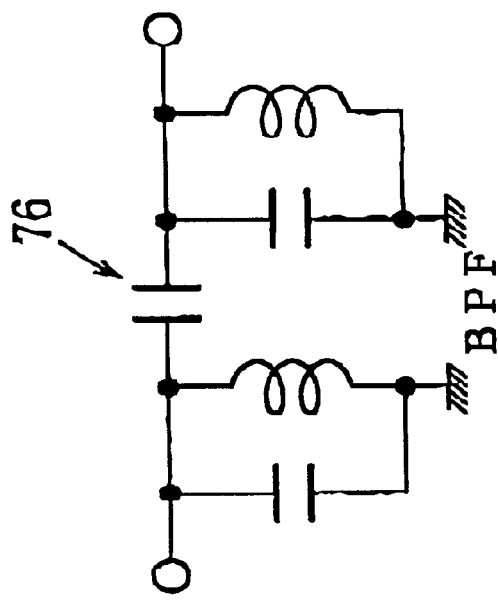
FIGS. 14(a)–14(c) illustrate circuits corresponding to the filter shown in FIG. 13.
Figure 14B:
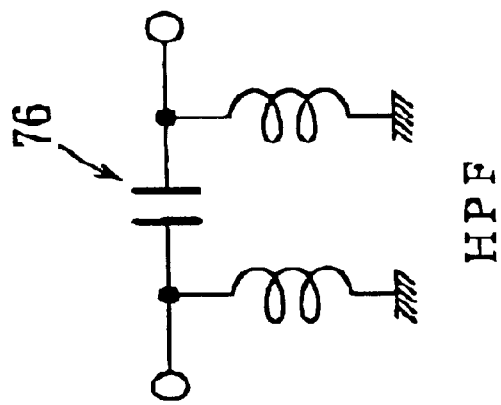
Figure 14A:
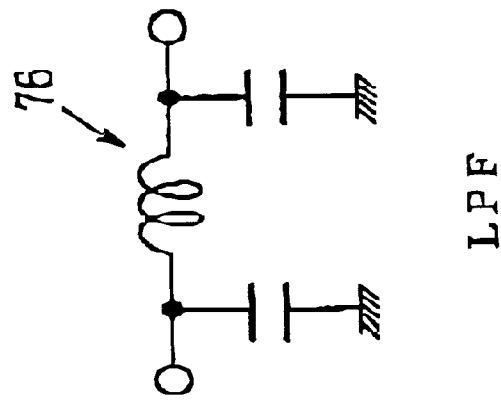

FIGS. 14(a)–(c) show several examples of a circuit for filter 76. FIG. 14 (a) is a typical low-pass filter (LPF) circuit; FIG. 14 (b) is a typical high-pass filter (HPF) circuit; and FIG. 14 (c) is a typical band-pass filter (BPF) circuit.

Figure 15:
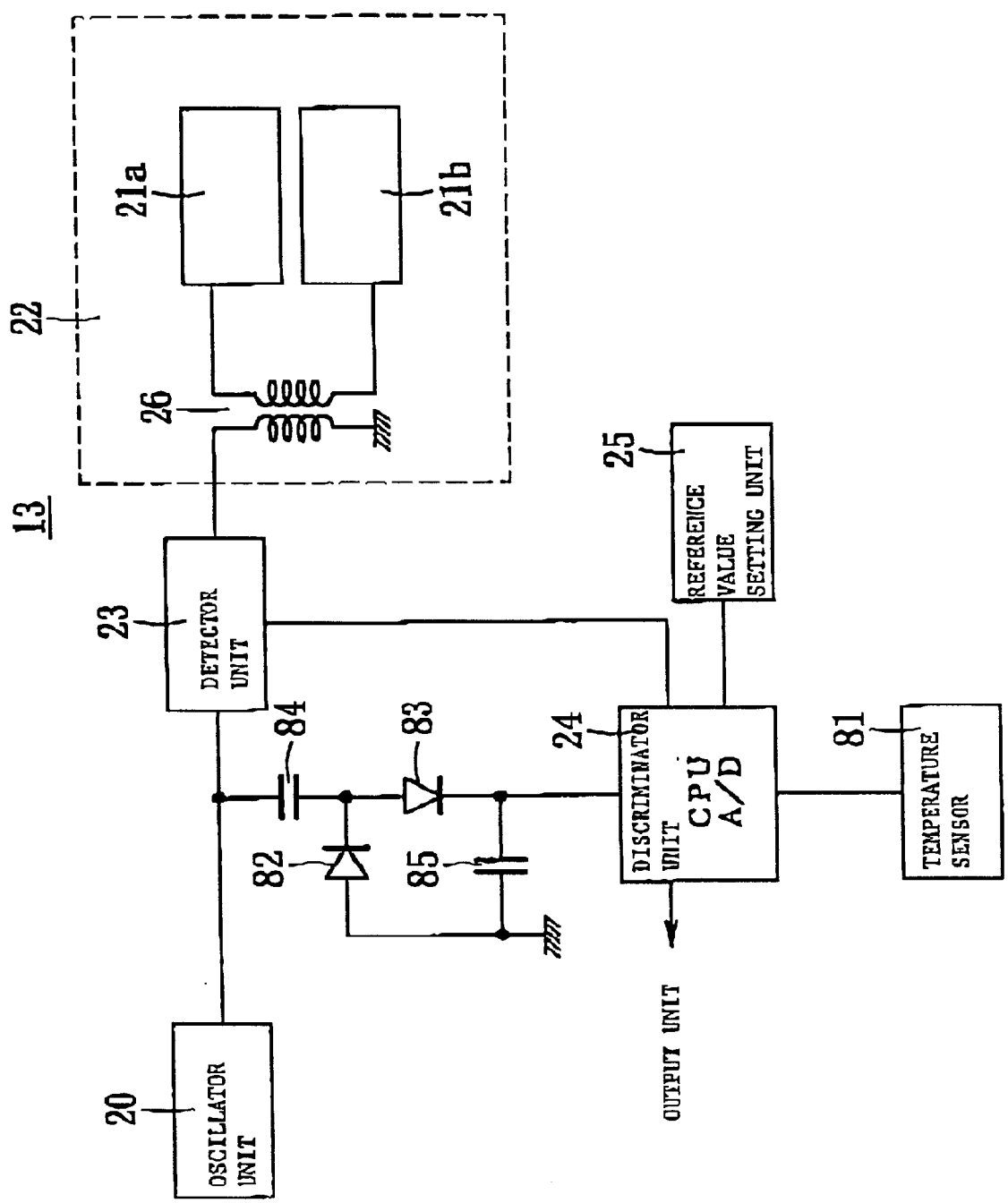
FIG. 15 illustrates a block diagram of another embodiment of the present invention.

FIG. 15 is an exemplary block diagram of a seventh preferred embodiment of a touch sensor. The output voltage of the diode in detector unit 23 which detects the wave varies with the ambient temperature. Here discriminator unit 24 uses the output of oscillator unit 20 as its reference voltage. Since this detector circuit uses the same diode as that used to detect the waveform in detector unit 23, it can perform in a stable fashion regardless of temperature variations. This embodiment has a temperature sensor 81 in discriminator unit 24. In response to an output signal from temperature sensor 81, the reference voltage from reference value setting unit 25 used in discriminator unit 24 is varied to correct for the temperature characteristics of the detector diode in detector unit 23. This makes the performance of detector unit 23 more stable.

FIG. 16 is an exemplary block diagram of an eight preferred embodiment of a touch sensor. This embodiment has an attenuator 86 between oscillator unit 20 and detector unit 23. The output of oscillator unit 20 normally remains stable in the face of changes in load impedance due to the presence of a human finger. When there is mismatching of the load impedance values, attenuator 86 mitigates the load-dependent variation of the output of oscillator unit 20 to ensure that the performance of the detector remains stable. Even with a substantial loss component, the attenuator 86 ensures that the oscillator unit 20 will perform in a stable fashion. However, since an excessive portion of the power going through will be lost if the loss fraction becomes too great, it is preferable to keep it at around 50%.

Figure 17:
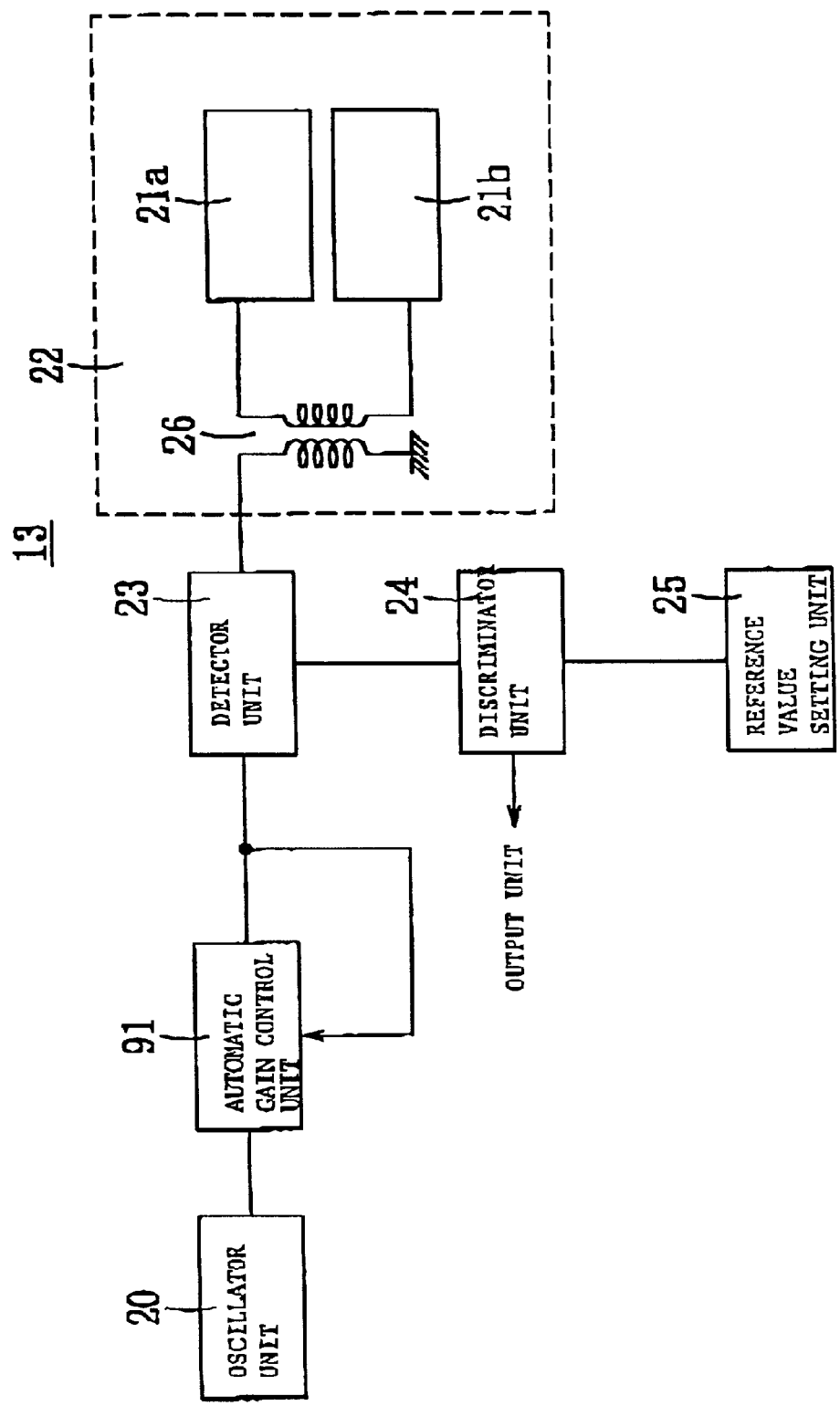
FIG. 17 illustrates a block diagram of another embodiment of the present invention.
Figure 18:
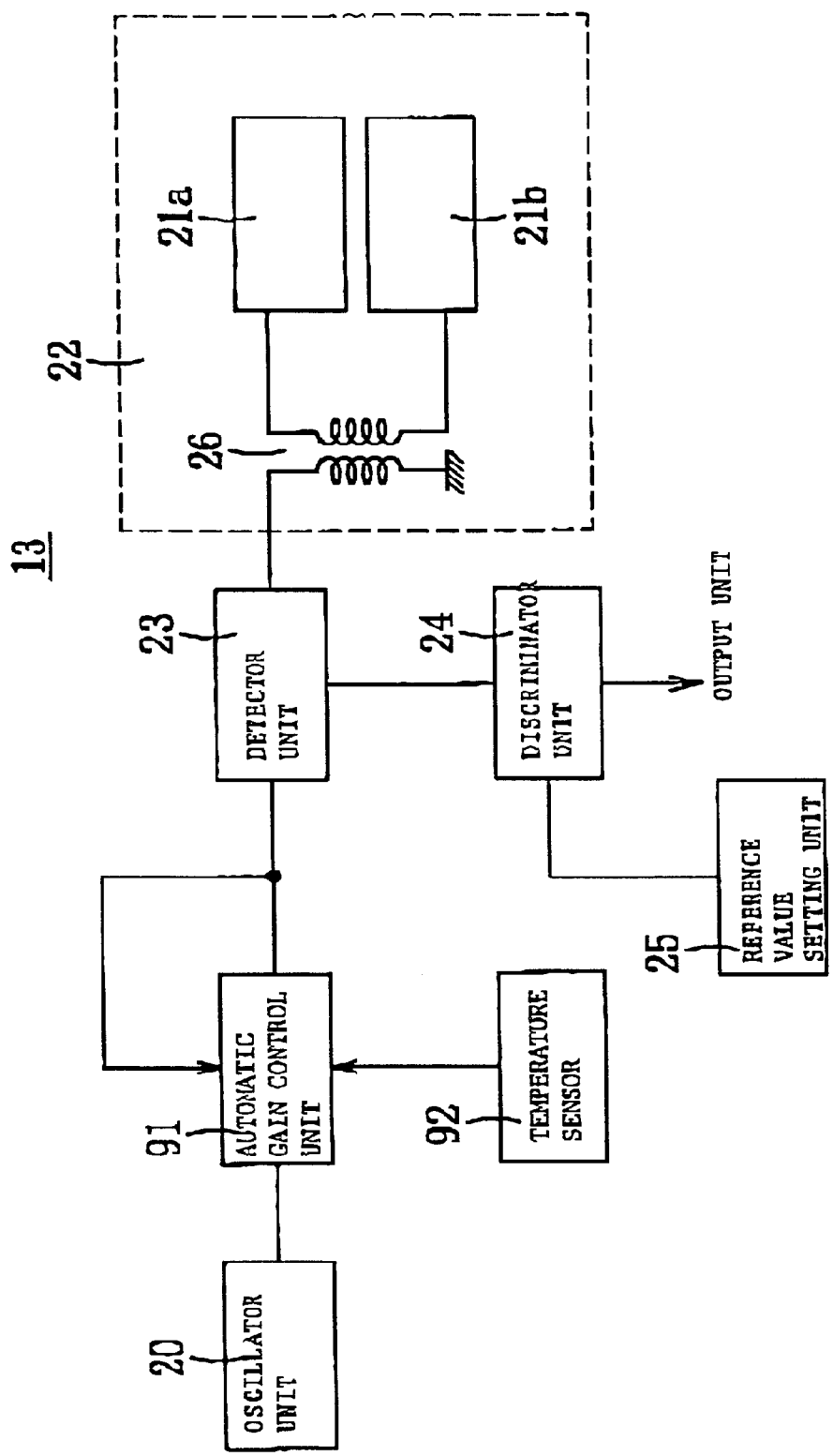
FIG. 18 illustrates a block diagram of another embodiment of the present invention.

FIG. 17 is an exemplary block diagram of a ninth preferred embodiment of a touch sensor used in the fingerprint identification device according to the present invention. This embodiment has an automatic gain control unit 91 between oscillator unit 20 and detector unit 23. Automatic gain control circuit 91 stabilizes the output of oscillator unit 20 and sends it to the electrode unit 22. This improves the accuracy of detection. FIG. 18 has a temperature sensor 92 in addition to the circuit shown in FIG. 17. To compensate for the temperature characteristics of the diode in detector unit 20, a temperature sensor 92 and an automatic gain control circuit 91 are provided. If the temperature drops, the output voltage of oscillator 20 is boosted. In this way the temperature related variation of the diode can be compensated for.

Figure 19:
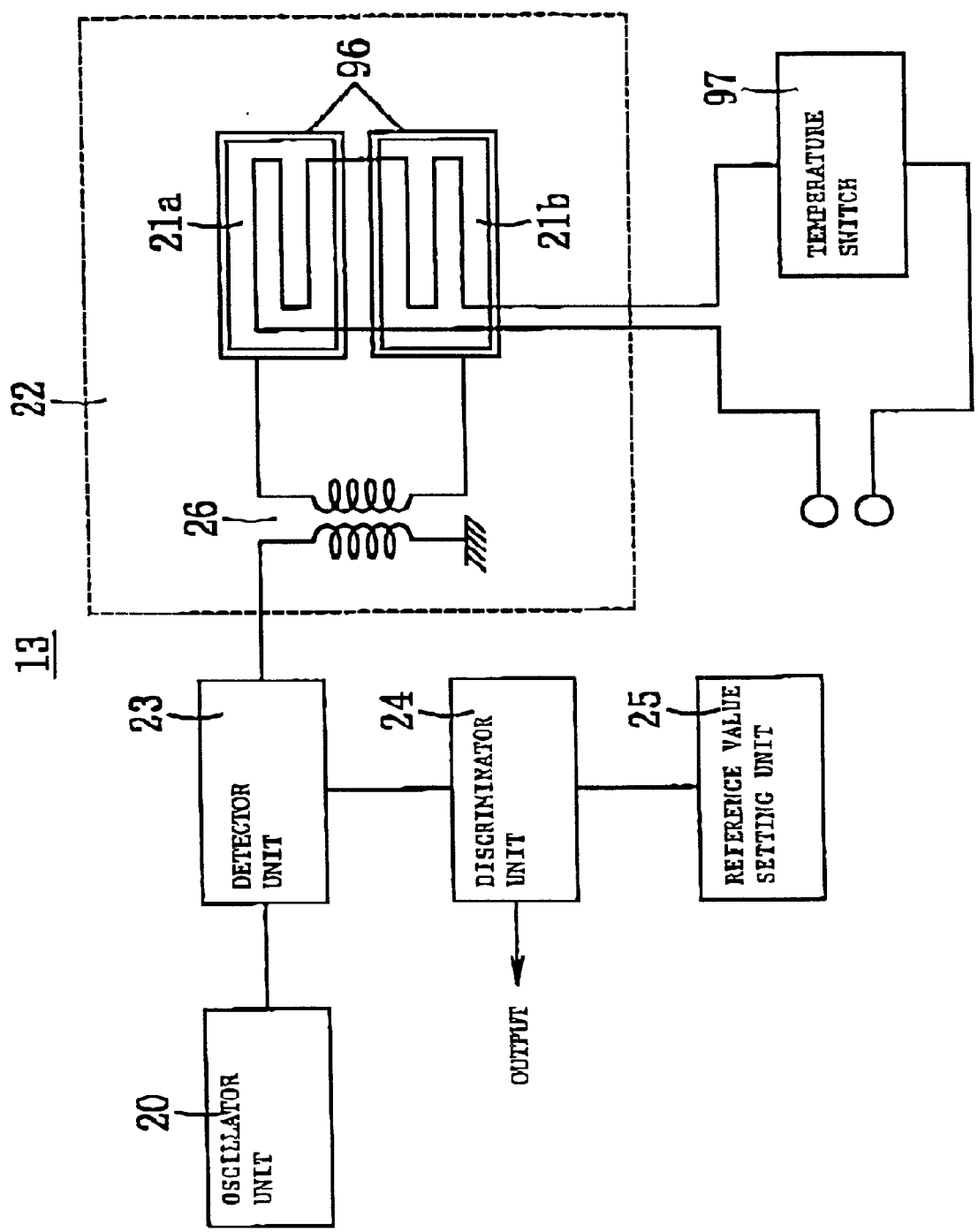
FIG. 19 illustrates a block diagram of another embodiment of the present invention.

FIG. 19 is an exemplary block diagram of a tenth preferred embodiment of a touch sensor. This embodiment has a heater 96 in electrode unit 22. Electrodes 21a and 21b are formed on top of heater 96. The temperature of electrodes 21a and 21b is kept constant by temperature switch 97. Electrode unit 22 is the location where a person is to touch the sensor. At temperatures below zero, however, it is unsafe to do so. Heater 96 and temperature switch 97 in electrode unit 22 allow the unit to be heated at low temperatures.

Figure 20:
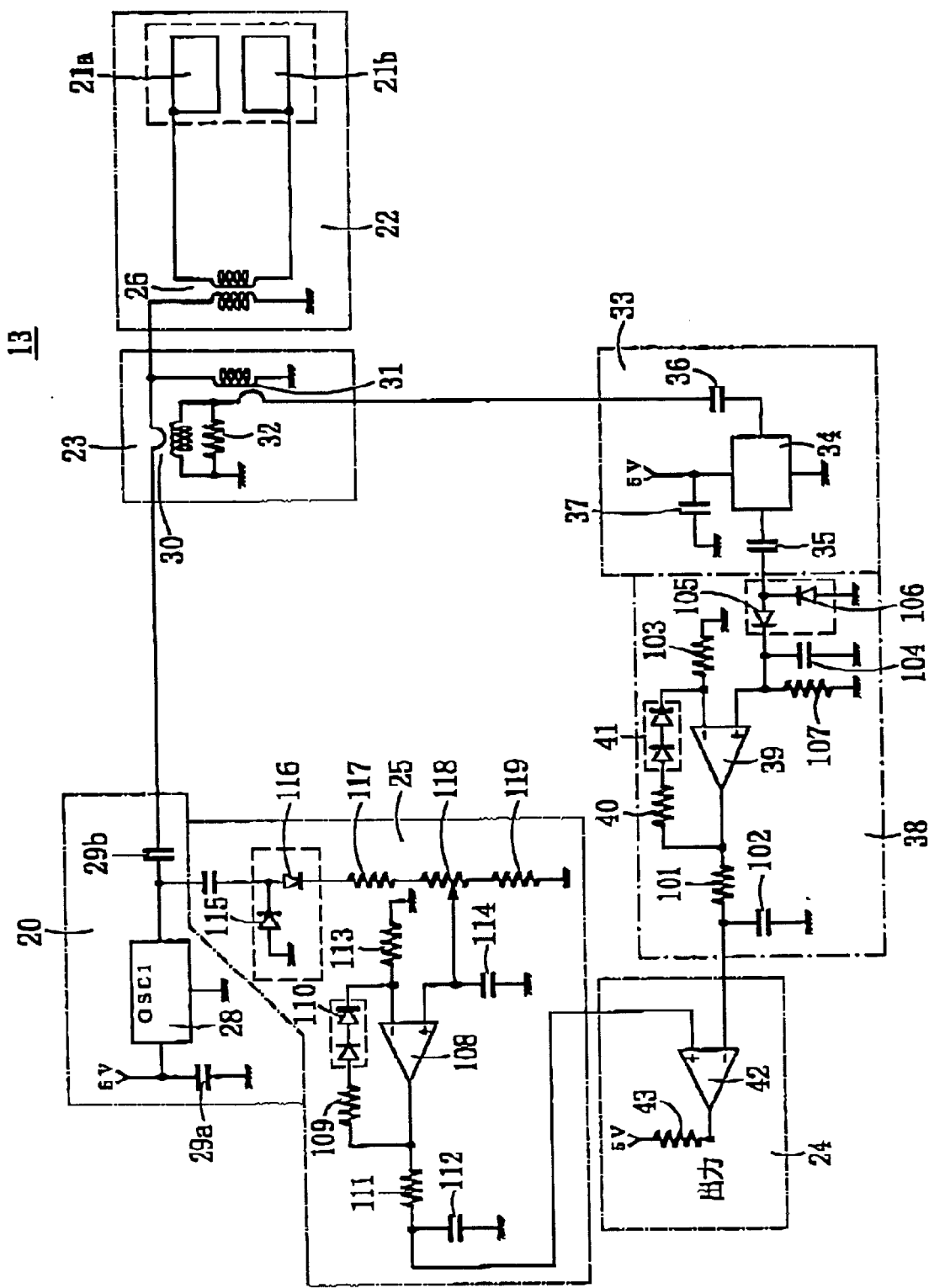
FIG. 20 illustrates another exemplary circuit diagram according to the present invention.

FIG. 20 illustrates an electric circuit of the fingerprint identification device according to this invention. The touch sensor 13 of this preferred embodiment differs from the same shown in FIG. 7 in reference value setting unit 25. Reference value setting unit 25 in this embodiment is configured by the same circuit as the demodulation amplifier circuit 38. Demodulation amplifier circuit 38 comprises operational amplifier 39, resister 40 and diode 41 in the negative feed back circuit provided between the output terminal and the reversing input terminal of the operational amplifier 39. The output terminal of operational amplifier 39 is connected with the input terminal of comparator 42 through resister 101. The output side of resister 101 is connected to the ground through condenser 102, and the reversing input terminal of operational amplifier 39 is connected to the ground through resister 103.

This configuration is also provided in reference value setting unit 25. In reference value setting unit 25, resister 109 and diode 110 in the negative feed back circuit provided between the output terminal and the reversing input terminal of the operational amplifier 108. The output terminal of operational amplifier 108 is connected with the input terminal of comparator 42 through resister 111. The output side of resister 111 is connected to the ground through condenser 112, and the reversing input terminal of operational amplifier 108 is connected to the ground through resister 113.

The output terminal of high-frequency amplifier circuit 33 is connected to the non-reversing input terminal of the operational amplifier 39 through detector diode 105. Detector diode 106 is provided between the anode of detector diode 105 and the ground. In reference value setting unit 25, the output signal from IC 28 in oscillator unit 20 is output through detector diode 116, and the output signal is divided by the dividing resisters 117–119, and then input into the non-reversing terminal of operational amplifier 108. Condenser 114 is provided between the non-reversing terminal and the ground.

Since the configuration of reference value setting unit 25 is basically same as the one for demodulation amplifier circuit 38, the temperature characters are also similar, and the temperature variation in the outputs can thus be offset.

In order to accelerate the temperature compensation, it is recommended that the detector diodes 115, 116 in reference value setting unit 25 are of the same type of diodes as detector diodes 105, 106 in demodulation amplifier circuit 38. Further, diode 110 provided in the negative feed back circuit of reference value setting unit 25 should be the same type as diode 41 provided in the negative feed back circuit of demodulation amplifier circuit 38. For the temperature compensation, the detector diodes in the detector and amplifier circuits other than demodulation amplifier circuit 38 can be of the same type as diode 115, 116 used in reference value setting unit 25.

Other embodiments of the invention will be apparent to those skilled in the art from a consideration of the specification and the practice of the invention disclosed herein. It is intended that the specification be considered as exemplary only, with the true scope and spirit of the invention being indicated by the following claims.

What is claimed is:

1. A fingerprint identification device equipped with a touch sensor for detecting a human finger, said touch sensor comprising:
   an oscillator which outputs a high-frequency signal;
   an electrode unit including a pair of electrodes which applies said high-frequency signal from said oscillator unit to the human finger;
   a detector unit which detects a variation of impedance values varied by said human finger contacting said pair of electrodes, and which outputs an output signal based on said variation of impedance values; and
   a discriminator unit which determines whether said human finger is in contact with said pair of electrodes by comparing said output signal from said detector unit with a predetermined reference value set in a reference value setting unit,
   wherein a capacitance between said human finger and said pair of electrodes increases when the human finger is in contact with said pair of electrodes, and a total resistance value of a high-frequency impedance real value of the human finger and a circuit resistance value including said pair of electrodes matches output impedance at a predetermined frequency of said oscillator, allowing said discriminator unit to determine that the contact is that of the human finger.

2. The fingerprint identification device according to claim 1, wherein the capacitance between the human finger and said pair of electrodes does not increase when the human finger is not in close contact with said pair of electrodes, the capacitance then decreases, and an imaginary component of an impedance value increases and does not match the output impedance at the predetermined frequency of said oscillator, thereby not allowing said discriminator unit to determine that the contact is that of the human finger.

3. The fingerprint identification device according to claim 1, wherein said pair of electrodes have symmetrical forms.

4. The fingerprint identification device according to claim 1, wherein said pair of electrodes are arranged in parallel.

5. The fingerprint identification device according to claim 1, wherein said electrode unit further comprises a transformer supplying electricity to said pair of electrodes, and matching a first impedance at a first side of said transformer to a second impedance at a second side of said transformer when the human finger makes contact with said pair of electrodes.

6. The fingerprint identification device according to claim 1, wherein said electrode unit further comprises an impedance converter circuit to supply electricity to said pair of electrodes, and to match an impedance when the human finger makes contact with said pair of electrodes.

7. The fingerprint identification device according to claim 1, wherein said pair of electrodes are provided in a detached sensor which is separated from other units of the touch sensor.

8. The fingerprint identification device according to claim 1, wherein said pair of electrodes are coated with a thin protective layer.

9. The fingerprint identification device according to claim 1, wherein said predetermined reference value of said impedance value between said pair of electrodes and the human finger is set at more than 500 PF.

10. The fingerprint identification device according to claim 1, wherein said pair of electrodes has a transmissivity which is set at more than 50%.

11. The fingerprint identification device according to claim 1, wherein said pair of electrodes comprise a high-frequency conductor.

12. The fingerprint identification device according to claim 1, wherein said pair of electrodes comprise a semiconductor having a high frequency loss.

13. The fingerprint identification device according to claim 1, wherein said high-frequency signal output by said oscillator is set between 0.1 and 300 MHz.

14. The fingerprint identification device according to claim 1, wherein said oscillator generates a plurality of high-frequency signals.

15. The fingerprint identification device according to claim 1, wherein said detector unit outputs a voltage value converted from a reflection wave power.

16. The fingerprint identification device according to claim 1, wherein said detector unit detects a voltage of said pair of electrodes thereby detecting if the human finger is in contact with said pair of electrodes.

17. The fingerprint identification device according to claim 1, wherein said detector unit further comprises a high-frequency amplifier.

18. The fingerprint identification device according to claim 1, wherein said detector unit further comprises a narrow-band high-frequency amplifier.

19. The fingerprint identification device according to claim 1, wherein said detector unit further comprises a filter to selectively pass high-frequency signals having different frequencies.

20. The fingerprint identification device according to claim 1, wherein said discriminator unit comprises a temperature compensating circuit including a diode which is identical to a diode used in said detector unit.

21. The fingerprint identification device according to claim 1, wherein said discriminator unit uses an output signal from said oscillator as a reference signal for discrimination.

22. The fingerprint identification device according to claim 21, wherein said reference signal from said oscillator is detected by a detecting element in said discriminator unit which is identical to an element used on said detector unit.

23. The fingerprint identification device according to claim 1, wherein said discriminator unit determines that the human finger is in contact with said pair of electrodes when said output signal from said detector unit is lower than a reference signal.

24. The fingerprint identification device according to claim 1, further comprising an attenuator between said oscillator and said detector unit.

25. The fingerprint identification device according to claim 24, wherein said attenuator passes half of the input power sent from said oscillator.

26. The fingerprint identification device according to claim 1, further comprising an automatic gain control unit between said oscillator and said detector unit.

27. The fingerprint identification device according to claim 1, further comprising an automatic gain control unit and a temperature sensor between said oscillator and said detector unit, for controlling the gain depending on an ambient temperature.

28. The fingerprint identification device according to claim 1, further comprising a heater to heat said pair of electrodes and to keep said pair of electrodes at a constant temperature.

29. The fingerprint identification device according to claim 1, wherein said detector unit outputs a voltage value converted from an SWR value.

30. The fingerprint identification device according to claim 1, wherein said detector unit detects a current output of said pair of electrodes thereby detecting if the human finger is in contact with said pair of electrodes.

31. The fingerprint identification device according to claim 1, wherein said predetermined reference value is within a predetermined range.

32. The fingerprint identification device according to claim 1, wherein said output signal is within a predetermined range.

33. The fingerprint identification device according to claim 1, comprising:
- a first unit applying a high frequency signal to an object and detecting multiple impedance values, and outputting a signal based on the multiple impedance values; and
- a second unit determining whether the object is in contact with electrodes of the first unit by comparing the signal with a predetermined reference value.

34. The method of sensing a human finger, comprising:

outputting a high-frequency signal from an oscillator unit;

applying said high-frequency signal to the human finger;

detecting a variation of impedance values varied by said human finger contacting a pair of electrodes, and outputting an output signal based on said variation of impedance values; and determining whether the human finger is in contact with said pair of electrodes by comparing said output signal with a predetermined reference value, wherein a capacitance between said human finger and said pair of electrodes increases when the human finger is in contact with said pair of electrodes, and a total resistance value of a high-frequency impedance real value of the human finger and a circuit resistance value including said pair of electrodes matches output impedance at a predetermined frequency of said oscillator unit, allowing the determining that the contact is that of the human finger.

35. The method of sensing an object, comprising:

applying a high frequency signal to the object which is in proximity of a pair of electrodes, and detecting a variation of impedance values varied by said object contacting said pair of electrodes, and outputting a signal based on the variation of impedance values; and determining whether the object is in contact with the electrodes by comparing the signal with a predetermined reference value, wherein a capacitance between said object and said pair of electrodes increases when the object is in contact with said pair of electrodes, and a total resistance value of a high-frequency impedance real value of the object and a circuit resistance value including said pair of electrodes matches output impedance at a predetermined frequency of said high frequency signal, allowing the determining that the contact is that of the object.

* * * * *